United States Patent
Fiset

(10) Patent No.: US 7,819,910 B2
(45) Date of Patent: Oct. 26, 2010

(54) SKIN TANNING AND LIGHT THERAPY SYSTEM

(75) Inventor: Peter Depew Fiset, Loudonville, NY (US)

(73) Assignee: LEDeep LLC, Loudonville, NY (US)

( * ) Notice: Subject to any disclaimer, the term of this patent is extended or adjusted under 35 U.S.C. 154(b) by 707 days.

(21) Appl. No.: 10/558,092

(22) PCT Filed: May 25, 2004

(86) PCT No.: PCT/US2004/014527

§ 371 (c)(1), (2), (4) Date: Nov. 23, 2005

(87) PCT Pub. No.: WO2004/105859

PCT Pub. Date: Dec. 9, 2004

(65) Prior Publication Data

US 2006/0271132 A1 Nov. 30, 2006

Related U.S. Application Data

(60) Provisional application No. 60/473,237, filed on May 24, 2003, provisional application No. 60/552,018, filed on Mar. 9, 2004.

(51) Int. Cl.
*A61N 5/06* (2006.01)

(52) U.S. Cl. .................... 607/91; 607/88; 607/90

(58) Field of Classification Search ............ 607/88–94; 606/9, 10; 128/898
See application file for complete search history.

(56) References Cited

U.S. PATENT DOCUMENTS

| | | | |
|---|---|---|---|
| 4,309,616 A | 1/1982 | Wolff | |
| 4,469,102 A | 9/1984 | Fish | |
| 4,703,184 A * | 10/1987 | Wolff | ............... 607/94 |
| 4,839,513 A | 6/1989 | Wijtsma | |
| 4,858,609 A | 8/1989 | Cole | |
| 5,374,825 A * | 12/1994 | Doty et al. | ............ 250/372 |
| 5,601,619 A | 2/1997 | Drechsler | |
| 5,913,883 A | 6/1999 | Alexander et al. | |
| 6,084,250 A | 7/2000 | Justel et al. | |
| 6,207,229 B1 | 3/2001 | Bawendi et al. | |
| 6,290,713 B1 | 9/2001 | Russell | |
| 6,322,901 B1 | 11/2001 | Bawendi et al. | |
| 6,350,275 B1 | 2/2002 | Vreman et al. | |
| 6,423,551 B1 | 7/2002 | Weiss et al. | |
| 6,447,537 B1 | 9/2002 | Hartman | |

(Continued)

FOREIGN PATENT DOCUMENTS

DE 198 52 524 A1 5/2000

(Continued)

OTHER PUBLICATIONS

U.S. Appl. No. 10/591,960, filed Mar. 9, 2005, Fiset, Peter D.

(Continued)

*Primary Examiner*—Ahmed M Farah
(74) *Attorney, Agent, or Firm*—Foley & Lardner LLP

(57) ABSTRACT

A system and method for at least one of skin tanning and phototherapy are provided. The system includes a chamber adapted for at least one of skin tanning and phototherapy and a nanostructure UV light emitting device.

10 Claims, 5 Drawing Sheets

U.S. PATENT DOCUMENTS

| | | |
|---|---|---|
| 6,452,217 B1 | 9/2002 | Wojnarowski et al. |
| 6,461,376 B1 | 10/2002 | Beshore |
| 6,494,900 B1 * | 12/2002 | Salansky et al. .............. 607/89 |
| 6,515,314 B1 | 2/2003 | Duggal et al. |
| 6,585,947 B1 | 7/2003 | Nayfeh et al. |
| 6,596,016 B1 | 7/2003 | Vreman et al. |
| 6,602,275 B1 | 8/2003 | Sullivan |
| 6,616,447 B1 | 9/2003 | Rizoiu et al. |
| 6,621,211 B1 | 9/2003 | Srivastava et al. |
| 6,828,576 B2 | 12/2004 | Spivak |
| 6,861,658 B2 * | 3/2005 | Fiset ...................... 250/504 R |
| 6,906,463 B2 | 6/2005 | Hildenbrand et al. |
| 7,001,414 B2 * | 2/2006 | Unvert et al. ................. 607/91 |
| 7,239,072 B2 * | 7/2007 | Snijkers-Hendrickx et al. .. 313/493 |
| 7,254,151 B2 * | 8/2007 | Lieber et al. ............. 372/44.01 |
| 7,294,417 B2 * | 11/2007 | Ren et al. ................... 428/701 |
| 7,306,620 B2 * | 12/2007 | Cumbie ...................... 607/88 |
| 2001/0053856 A1 | 12/2001 | Leduc et al. |
| 2002/0074559 A1 | 6/2002 | Dowling et al. |
| 2002/0127224 A1 | 9/2002 | Chen |
| 2002/0161418 A1 | 10/2002 | Wilkens et al. |
| 2002/0173833 A1 | 11/2002 | Korman et al. |
| 2002/0183811 A1 | 12/2002 | Irwin |
| 2003/0003300 A1 | 1/2003 | Korgel et al. |
| 2003/0034486 A1 | 2/2003 | Korgel et al. |
| 2003/0044114 A1 | 3/2003 | Pelka |
| 2003/0044365 A1 | 3/2003 | Candau et al. |
| 2003/0045916 A1 | 3/2003 | Anderson et al. |
| 2003/0161795 A1 | 8/2003 | Tsuzuki et al. |
| 2003/0167080 A1 | 9/2003 | Hart et al. |
| 2003/0216795 A1 | 11/2003 | Harth et al. |
| 2004/0015214 A1 | 1/2004 | Simkin et al. |
| 2004/0036130 A1 | 2/2004 | Lee et al. |
| 2004/0075065 A1 | 4/2004 | Spivak |
| 2004/0076926 A1 | 4/2004 | Baughman |
| 2004/0175337 A1 | 9/2004 | Richard et al. |
| 2004/0252488 A1 * | 12/2004 | Thurk ........................ 362/147 |
| 2005/0042187 A1 | 2/2005 | Verma et al. |
| 2005/0187596 A1 | 8/2005 | Fiset |
| 2005/0201963 A1 * | 9/2005 | Dutta ........................ 424/70.1 |
| 2006/0155349 A1 | 7/2006 | Kemeny et al. |
| 2006/0273328 A1 * | 12/2006 | Niu et al. ...................... 257/79 |
| 2007/0274909 A1 * | 11/2007 | Justel et al. ................. 424/1.53 |
| 2007/0276455 A1 * | 11/2007 | Fiset .......................... 607/91 |
| 2008/0039907 A1 | 2/2008 | Fiset |
| 2009/0057650 A1 * | 3/2009 | Lieber et al. .................. 257/24 |

FOREIGN PATENT DOCUMENTS

| | | |
|---|---|---|
| EP | 1 197 478 A1 | 4/2002 |
| WO | WO 95/24888 A1 | 9/1995 |
| WO | WO 2005/086846 A2 | 9/2005 |
| WO | WO 2005/117828 A2 | 12/2005 |

OTHER PUBLICATIONS

Supplementary Partial European Search Report dated Dec. 7, 2009, in corresponding EP 04751757.8, 4 pages.

Supplementary European Search Report dated Dec. 17, 2009, in corresponding EP 05751907.6, 5 pages.

Green et al., "311 nm UVB phototherapy—an effective treatment for psoriasis," British Journal of Dermatology, Dec. 1, 1988, 119(6):691-696.

Ozawa et al., "312-nanometer Ultraviolet B Light (Narrow-Band UVB) Induces Apoptosis of T Cells within Psoriatic Lesions," J. Exp. Med., Feb. 15, 1999, 189(4):711-718.

Wang et al., "Multilayer waveguide-grating filters," Applied Optics, May 10, 1995, 34(14):2414-2420.

* cited by examiner

SKIN TANNING AND LIGHT THERAPY SYSTEM

The present application claims benefit of U.S. Provisional Patent Application Ser. No. 60/473,237, filed May 24, 2003, U.S. patent application Ser. No. 10/714,824 filed Nov. 17, 2003 and U.S. Provisional Patent Application Ser. No. 60/552,018, filed Mar. 9, 2004, which are incorporated by reference in their entirety.

FIELD OF THE INVENTION

The present invention is directed generally to tanning and phototherapy systems and specifically to systems which incorporate nanostructure UV radiation sources.

BACKGROUND OF THE INVENTION

The most common method of skin tanning involves the process of exposing skin to ultra-violet light. Health research has shown that both the condition of under-exposure to ultra-violet light and the condition of over-exposure to ultra-violet light causes a variety of health problems. Health research has also shown that specific ranges of wavelengths of ultra-violet light are responsible for producing health benefits. Moderate exposure to specific wavelengths of ultra-violet light produces the greatest benefits with the least amount of health risk. Certain methods and devices are useful at controlling the quantity and quality of ultra-violet light exposure in the effort to produce the greatest health benefits with the least amount of health risks. Ultra-violet light quality depends primarily on the ranges of wavelength of ultra-violet light; where the highest ultra-violet light quality is the ultra-violet light that produces the greatest net health benefits.

The sun is a primary source of ultra-violet light for tanning. The quantity of light exposure to the sun is simple to control. The quality of ultra-violet light exposure by the sun is not simple to control. Lamps that provide alternative sources of ultra-violet light allow for tanning services that do not rely on the sun. These tanning services are available and are administered in a controlled environment such as in personal care service salons. The industry providing controlled exposure to artificial ultra-violet light is generally referred to as the "indoor-tanning" industry. Indoor-tanning does not implement systems that are directly dependent on the sun as the source of ultra-violet radiation. The quality of the indoor-tanning ultra-violet light has become important in differentiating services available within the same indoor-tanning salon and between competing tanning salons.

Light with wavelengths in the ultra-violet range is often referred to as UV light or UV. UVA, UVB and UVC describe three separate non-overlapping but adjacent ranges of light fully encompassing the UV light range. The range of light referred to as UVA generally has the longest set of wavelengths within the UV range and includes wavelengths between 290 and 400. UVA-1 is between 340 and 400; UVA-2 is between 290 and 340; and UVA-3 is between 290 and 310. The range of light referred to as UVC generally has the shortest set of wavelengths within the UV range and includes wavelengths between 160 and 260. The range of light referred to as UVB includes wavelengths between 260 and 290.

The use of the terms UVA, UVB and UVC allow the various properties of UV light to be categorized in general ways. UVA has the best capability of tanning skin. UVB does not produce a tan in the third layer of skin. UVC light does not produce a tan but can sterilize some biological agents such as certain bacteria. Under certain conditions UVB will tan the second layer of skin. The second layer of skin when tanned with UVB has a shedding period of 5 to 8 days. Skin tanned with UVA only has the third layer of skin tanned which results in a normal shedding cycle of 28 days.

Under normal conditions the outer layer of skin, also known as the first layer, is composed of dead cells. Normally, dead cells will not produce melanin upon exposure to moderate amounts of UV. The layer under the first layer of skin is referred to as the second layer of skin, and is composed of active cells that may be functioning in some biological manner and will produce melanin upon exposure to UVB light. UVB skin tanning has, what some tanners consider, an additional negative effect, UVB tanning will thicken the second layer of skin and as a result increases the visibility of skin lines and wrinkles. UVB tanning creates a shedding cycle of 5 to 7 days which is undesirable when a UVA tan has a shedding cycle of 28 days. When UVB is combined with UVA the shedding cycle of the UVA tanned layer is accelerated since the second layer is shed more quickly and the third layer becomes the second layer as a result and is shed within another 5 to 7 days.

Under normal conditions the layer of skin that will produce melanin when exposed to UVA light is referred to as the third layer of skin. In exceptional conditions such as albinism, the third layer of skin is not capable of producing melanin. For the purposes of this application, albino skin is considered an exception to the norm and will not be referred to as a third layer of skin but as an albino third layer of skin.

It is common knowledge that all wavelengths of UV over long exposure periods damages the skin in various ways. Therefore, it is desirable to limit the exposure of UV radiation to skin. Alternatively, some UV exposure is generally considered necessary in order to maintain good health in other bodily functions, such as the generation of vitamin-D. Vitamin-D is useful in the absorption of calcium in the body. Therefore, it has been recommended by various health organizations studying the phenomena that moderate exposure to UV light has a net health benefit, whereas over-exposure or under-exposure of UV results in a net health deficit. The art of indoor-tanning to remain useful should provide for ever increasing controllability of the application of the light therapy. As a light therapy tanning should be applied with specific goals and procedures to maximize the benefits of the therapy.

For people desiring a tan, the main benefits of UV exposure is the production of tanned skin. Tanners enjoy positive psychological and perceived positive social benefits resulting from having tanned skin. In order to limit the total amount of UV radiation tanners are exposed to while maintaining a tan, it is desirable to reduce as much as possible the exposure to UV light outside the UVA wavelength range. UVB and UVC wavelength ranges of radiation are by definition not capable of tanning skin with a 28 day shedding cycle and therefore reasonable efforts should be made to eliminate UVB and UVC from the source of light tanners are exposed to.

Indoor-tanning methods generate UV light from converting electrical energy to light within devices such as UV fluorescent bulbs and high and low pressure mercury vapor bulbs are two specific types of light bulb technologies. UV light bulbs currently in use have properties of high voltage, high temperature, and low electrical energy to UV conversion efficiencies under seventeen percent.

Within the fluorescent light bulb category there are a variety of types that differ mainly in the percentage of UV light produced in the UVA, UVB and UVC wavelength ranges. For tanners concerned with overexposure to UV light the more desirable fluorescent bulbs have a higher percentage of light in the UVA-1 wavelength range. Tanners concerned with overexposure prefer and tend to pay a premium for tanning services that have the least amount of UVB and UVC.

Depending on weather conditions, typically 88% of the UV radiation from the sun is UVA, in this case an artificial source with more than 88% of the UV radiation is UVA is considered a safer tanning method than sun-tanning. Common fluorescent tanning bulbs and associated services have UV composed between 92.0% UVA to 97.5% UVA. Currently, high pressure quartz metal-halogenide bulbs have in general 98.5% UVA and are considered to be the least harmful artificial tanning bulbs currently used in indoor-tanning salons.

BRIEF SUMMARY OF THE INVENTION

A preferred embodiment of the present invention provides a system for at least one of skin tanning and phototherapy, comprising a chamber adapted for at least one of skin tanning and phototherapy, and a nanostructure UV light emitting device.

Another preferred embodiment of the present invention provides a system for at least one of skin tanning and phototherapy, comprising a first means for at least one of skin tanning and phototherapy, and a nanostructure UV light emitting device.

Another preferred embodiment of the present invention provides a method for at least one of skin tanning and phototherapy, comprising providing UVA light from a nanostructure UV light emitting device onto a skin of a human subject who is located in a chamber adapted for at least one of skin tanning and phototherapy in order to at least one of tan the skin and to provide phototherapy for the skin.

DETAILED DESCRIPTION OF THE PREFERRED EMBODIMENTS

Figure 1A:
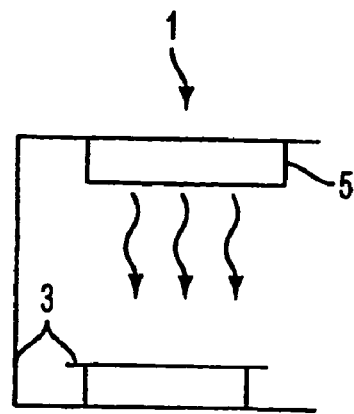
FIGS. 1A and 1B are schematic side views of systems according to embodiments of the present invention.
Figure 1B:
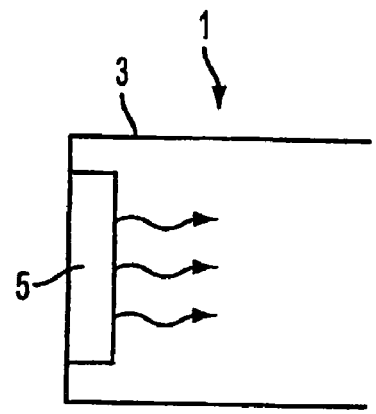

The present inventor has realized that a system for at least one of skin tanning and phototherapy may use a nanostructure UV light emitting device. This allows a control of the peak wavelength of the UV light as well as provides UV light with a narrow wavelength distribution (i.e., a narrow peak width). FIGS. 1A and 1B illustrate the system 1 which contains a chamber 3 adapted for at least one of skin tanning and phototherapy and the nanostructure UV light emitting device 5. The system 1 may be used solely for skin tanning or for phototherapy or for both skin tanning and phototherapy depending on the need of the person being subjected to the UV light. FIG. 1A illustrates an indoor tanning or phototherapy system for the prone body position, which is commonly referred to as a tanning or a phototherapy bed. FIG. 1B illustrates an indoor tanning or phototherapy system for upright body positions, which is commonly referred to as a tanning or a phototherapy booth.

The nanostructure UV light emitting device comprises at least one of a nanoparticle and a nanowire UV light emitting device. Preferably, the UV light emitting device emits only UVA light. The term UV light includes radiation having a peak wavelength between 160 and about 400 nm rather than visible light having a wavelength between above about 400 and below about 700 nm. UVA light has a peak wavelength between about 290 and about 400 nm. The nanoparticles and nanowires emit light (i.e., radiation) with a very narrow peak width due to their size rather than due to their chemical composition. Thus, in contrast to conventional ceramic phosphors which emit light with a broad peak width due to their chemical composition and activator ion content, nanoparticles and nanowires emit light with varying peak wavelength due to varying their size (i.e., diameter or thickness). Furthermore, some materials, such as silicon, which ordinarily do not emit light in bulk form, emit light in nanoparticle form due to the nanoparticle size. Thus, the nanoparticle or nanowire size may be selected such that the nanoparticles or nanowires emit only UVA light, but no UVB light. Furthermore, nanoparticle or nanowire size may be selected such that the nanoparticles or nanowires emit only UVA-1, UVA-2 and/or UVA-3 light depending on the desired effect, since the peak width of the emitted UV light is narrow.

Nanoparticles may be any suitable nanoparticles, such as nanocrystals or quantum dots, having a diameter less than 100 nm, such as a diameter of 2-20 nm, for example. For example, metal, semiconductor, as well as metal or semiconductor oxide and/or nitride nanoparticles may be used. Semiconductor nanoparticles include materials from Groups IV (Si, Ge, SiC, SiGe), II-VI (CdS, ZnS, CdSe, ZnSe, ZnTe, CdTe), IV-VI (PbS, PbSe, PbTe) or III-V (GaAs, GaP, GaN, InP, InAs). Ternary and quaternary semiconductor nanoparticles, such as CdZnS, CdZnSe, CdZnTe, CdZnTeSe, CdZnSSe, GaAlAs, GaAlP, GaAlN, GaInN, GaAlAsP and GaAlInN for example, may also be used. Ceramic or metal oxide nanoparticles may also be used, such as silica, alumina, titania, zirconia, yttria stabilized zirconia, yttria, ceria, spinel (for example, $MgO*Al_2O_3$) and tantalum pentoxide, as well as other suitable ceramics having a more complex structure, such as radiation emitting phosphors (for example, YAG:Ce ($Y_3Al_5O_{12}$:Ce) and various halophosphate, phosphate, silicate, aluminate, borate and tungstate phosphors) and scintillators (for example, LSO, BGO, YSO, etc.). Other metal oxide nanoparticles, such as zinc oxide, indium oxide or indium tin oxide or metal nitride nanoparticles, such as aluminum nitride may also be used. Metal nanoparticles may be pure metal or metal alloy nanoparticles, such as Al, Fe, Cu, Ni, Au, Ag, Pt, Pd, Ti, V, Ta, W, Mn, Zn, Mo, Ru, Pb, Zr, etc. and alloys thereof.

Other materials, such as Boron Carbide, Titanium Oxide (TiO), Silicon Carbide (SiC), Antimony (Sb), Arsenic (As), Bismuth (Bi), Cadmium (Cd), Carbon (C), Gallium (Ga), Germanium (Ge), Indium (In), Phosphorus (P), Selenium (Se), Sulfur (S), Tellurium (Te), Calcium (Ca), Chromium (Cr), Cobalt (Co), Magnesium (Mg), Tantalum (Ta), Silicon Arsenide Germanium Telluride (SiAsGeTe), Vanadium Oxide, Zinc Germanium Phosphide (ZnGeP2), Zinc Germanium Phosphide (ZnGeP), Aluminum Antimonide (AlSb), Aluminum Arsenide (AlAs), Aluminum Phosphide (AlP), Gallium Selenide (GaSe), Gallium Telluride (GaTe), Indium Antimonide (InSb) and Silicon Arsenide Telluride (SiAsTe) may also be used.

Nanoparticles may be provided in the UV light emitting device 5 in any suitable form. For example, the nanoparticles may be located as a solid layer or layers on a UV transparent and UV resistant material substrate. The solid layer may also contain a UV transparent and UV resistant binder or filler if desired. Alternatively, the nanoparticles may be located in a suspension. The fluid of the suspension may comprise any suitable UV transparent fluid. Preferably, the fluid comprises a fluorocarbon fluid, such as perfluorocarbon, chlorofluorocarbon or hydrofluorocarbon fluid. For example, the fluid may comprise 1,1,1,2 tetrafluoroethane also known as R134A or perfluorocarbon fluids sold under the PPx series from F2 Chemicals Ltd. in Lea Town, U.K., such as the PP6 perfluorocarbon fluid. The R134A fluid is provided under elevated pressure to remain in the liquid state at room temperature. Other fluids which are liquid at atmospheric pressure at room temperature may also be used. If the nanoparticles are located in a suspension, then the suspension is located in a sealed vessel or tube made of a UV transparent and UV resistant material. If desired, the device 5 may also contain a pump or vibrator which maintains the suspension under turbulent flow to prevent the nanoparticles from settling on the surface of the vessel.

Nanowires may be any suitable nanowires having a thickness (i.e., diameter) of less than 150 nm, such as a thickness of 70-100 nm, for example. The nanowires may comprise any suitable material, such as metal oxide material. For example, zinc oxide, indium oxide and indium tin oxide nanowires may be used. Any suitable length of nanowires may be used.

The system 1 further preferably comprises a UV excitation source 7. The source 7 is positioned to provide UV excitation radiation of a first peak wavelength onto the nanostructure UV light emitting device 5 to cause the nanostructure UV light emitting device to emit UVA light having a second UVA peak wavelength longer than the first peak wavelength. Any suitable UV excitation source may be used.

Figure 2:
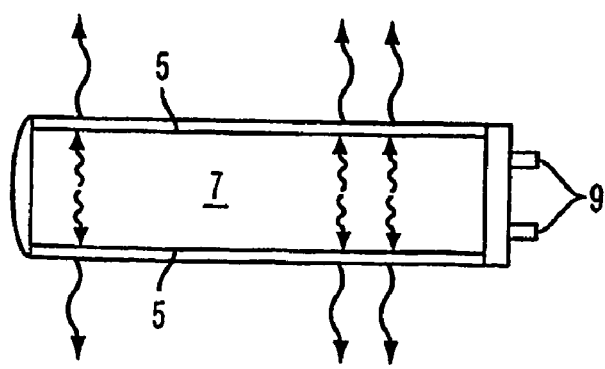
FIGS. 2, 3, 4A, 4B, 5 and 6 are cross sectional side views of nanostructure UV light emitting devices according to embodiments of the present invention.

In one preferred embodiment shown in FIG. 2, the UV excitation source 7 comprises a gas vessel comprising a gas which is adapted to emit the UV excitation radiation in response to a stimulus. For example, the source may be a gas lamp tube filled with a gas such as Ar or Hg which emits UV radiation when a voltage is applied to the electrodes 9 of the gas tube. The UV light emitting device 5 in this embodiment comprises at least one layer of nanoparticles coated on an inner surface of at least one UV light transparent wall of the gas vessel or tube 7. In other words, the conventional phosphor in a fluorescent lamp 7 is replaced with or combined with one or more layers of nanoparticles which emit UVA light in response to UV excitation radiation emitted by the gas. In this case, rather than using an expensive UV emitting lamp, a cheap germicidal or white light emitting lamp may be used instead, but with replacing the white light emitting phosphor with UVA light emitting nanoparticles. Preferably plural layers of nanoparticles are coated on the inner surface of the gas tube or vessel 7 to prevent the UVB or UVC radiation emitted by the gas, such as 254 nm UVC radiation, from being incident on the skin of a person in the tanning or phototherapy chamber 3. The UV exciting radiation from the gas in vessel 7 is incident on the nanoparticles 5, which emit UVA light in response to the incident radiation. The nanoparticles 5 block the UV excitation radiation, such as UVC radiation, from exiting the vessel or tube 7.

Figure 3:
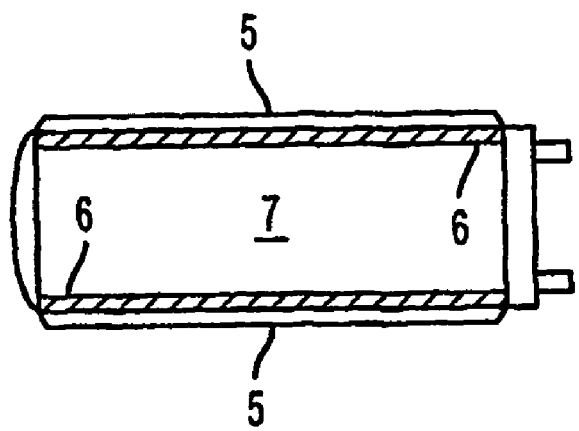

In another preferred embodiment shown in FIG. 3, the UV excitation source 7 comprises any suitable UV lamp which optionally contains a UV emitting phosphor 6 on its inner walls. The UV light emitting device 5 comprises at least one layer of nanoparticles coated on an outer surface of the UV lamp 7. The UV exciting radiation from the lamp from the lamp 7 is incident on the nanoparticles 5, which emit UVA light in response to the incident radiation.

Various other UV excitation sources 7 may be used. For example, the UV excitation source may comprise a focusing lens which focuses solar radiation onto the UV light emitting device. Furthermore, while an optical UV excitation source 7 is preferred, in an alternative aspect of the invention, an electrical excitation source may be used instead. In this case, the nanoparticles or nanowires 5 are located between two electrodes. At least one electrode is preferably made of an electrically conductive and UV transparent material, such as indium oxide, tin oxide or indium tin oxide (ITO). When a voltage is applied between the electrodes, the voltage causes the nanoparticles or nanowires to emit UV light.

It should be noted that the nanoparticles or nanowires 5 do not have to be placed directly on the UV excitation source 7. The nanoparticles or nanowires may be located on a separate substrate, such as a UV transparent substrate, or in a separate suspension in a vessel, which is located between the UV excitation radiation source 7 and the portion of the chamber 3 which houses the person undergoing tanning or phototherapy.

Figure 4A:
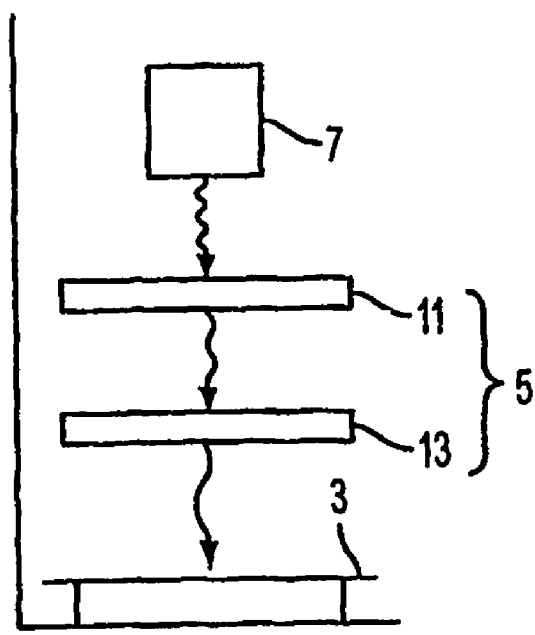

In a third embodiment shown in FIG. 4A, the UV light emitting device 5 comprises a plurality of layers of nanoparticles or nanowires arranged in a direction extending from the UV excitation radiation source 7 to the portion of the chamber 3 which houses the person undergoing tanning or phototherapy. The nanoparticles or nanowires in each layer emit radiation having a different peak wavelength from the nanoparticles or nanowires in other layers. Preferably, the peak wavelength of the UV radiation emitted by the nanoparticles or nanowires increases in each subsequent layer in the direction from the UV excitation source 7 to the portion of the chamber 3 which houses the person undergoing tanning or phototherapy. In other words, the nanoparticles or nanowires in each layer located closer to the person's skin (i.e., further from the UV excitation source 7) emit radiation of a longer wavelength that those in another layer located further from the person's skin (i.e., closer to the UV excitation source 7). This allows the stacked layers of nanoparticles or nanowires to gradually or stepwise upconvert the UVB and/or UVC radiation emitted by the UV excitation radiation source 7 to desired UVA radiation. There may be two or more layers of nanoparticles or nanowires.

For example, as shown in FIG. 4A, the UV excitation radiation source 7 may emit 254 nm peak UVC radiation. A first layer 11 of first nanoparticles or nanowires is located proximal to the UV excitation source 7. The first nanoparticles or nanowires emit UV light of a third peak wavelength, such as 315-340 nm, which is longer than the 254 nm peak wavelength, when irradiated with the UV excitation radiation from source 7. A second layer 13 of second nanoparticles or nanowires is located distal from the UV excitation source, such that the first layer 11 is located between the second layer 13 and the UV excitation source 7. The second nanoparticles or nanowires emit UV light of the second peak wavelength longer than the third peak wavelength when irradiated with the UV light from the nanoparticles or nanowires of the first layer 11. For example, the nanoparticles or nanowires of the second layer 13 may emit UVA-1 radiation having a peak wavelength of 345-355 nm or 395-405 nm when irradiated with UVA-2 or UVA-3 radiation from the first layer 11. Additional layers of nanoparticles or nanowires may be located between layers 11 and 13 to make the radiation wavelength upconversion (i.e., energy down conversion) even more gradual.

Layers 11, 13 may be formed directly on each other with the UV excitation source 7 acting as a substrate. Alternatively, each layer 11, 13 may be spaced apart from the adjacent layer and each layer may be formed on a separate UV transparent substrate, such as glass, plastic or quartz substrate, or in a separate solution holding vessel.

Figure 4B:
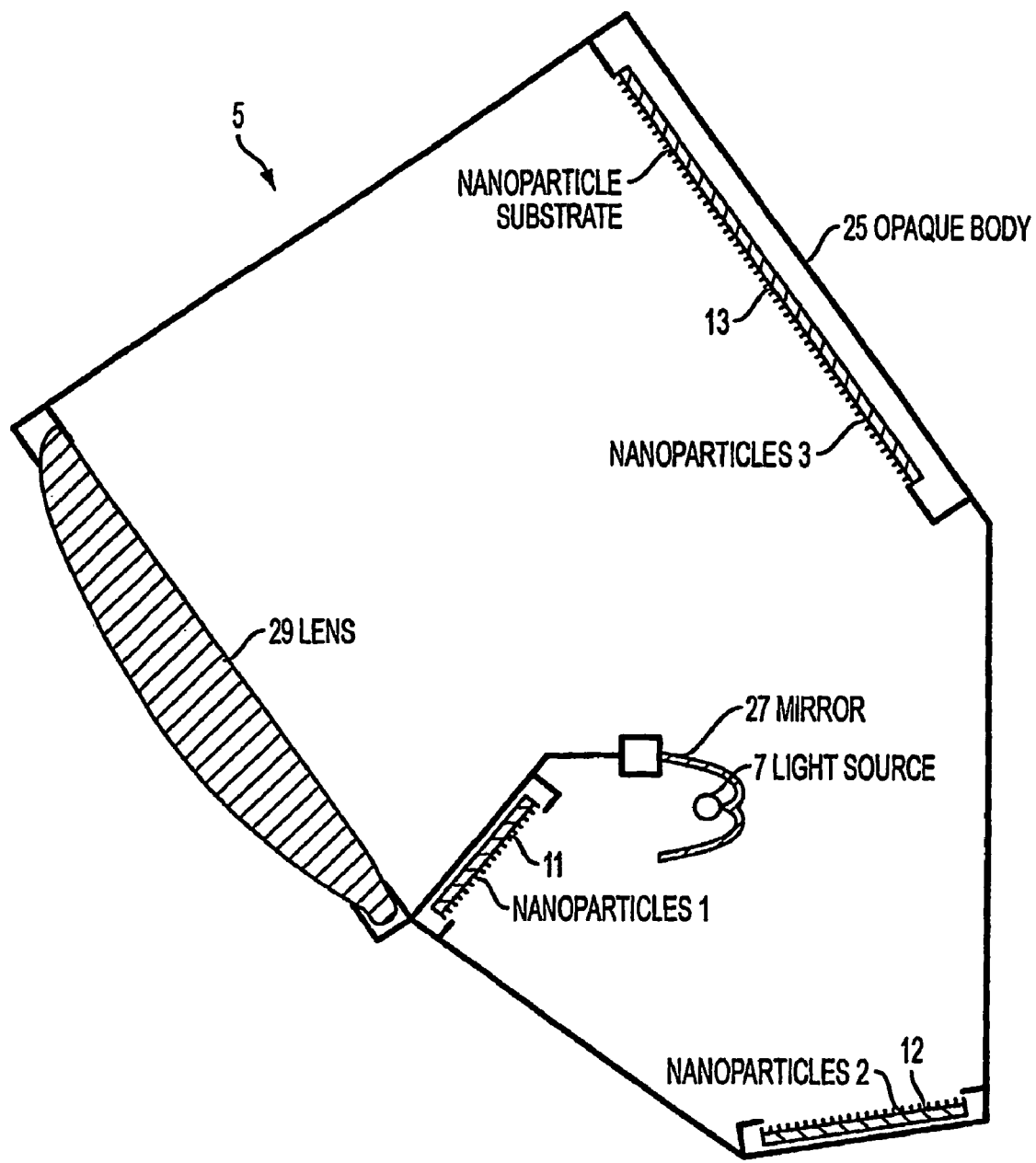

FIG. 4B illustrates an alternative aspect of the third embodiment. In this aspect, three layers of nanoparticles or nanowires 11, 12 and 13 are arranged in a clam-shell type housing 25 comprising an opaque body. The UV excitation source 7 is located in the interior portion of the housing 25. A mirror 27 shields the back side of the source 7. The first layer 11 of nanoparticles or nanowires is located opposite to the source 7 and mirror 27, such that UV excitation radiation from source 7 and mirror 27 is incident on the first layer 11. The second layer 12 of nanoparticles or nanowires emits UV light having a peak wavelength between those of the first 11 and third 13 layers. The second layer 12 is positioned in the housing to receive UV light from the first layer 11 and to emit UV light of a longer wavelength onto the third layer 13. The third layer 13 is positioned to receive UV light from the second layer 12 and to emit UV light of an even longer wavelength out of the housing through a lens 29 and through an optional long wavelength filter, which blocks shorter wavelength UV light from the source 7, first layer 11 and second layer 12 from exiting the housing 25. If desired, a light absorbing surface may be located behind the layers 11, 12 and 13. It should be noted that the term "layer" as used herein includes a nanoparticle or nanowire solid layer as well as a nanoparticle suspension located in a vessel. By using the clam-shell shaped housing 25, UV light of one or more desired wavelengths from layers 11, 12 and/or 13 exits the housing 25.

Figure 5:
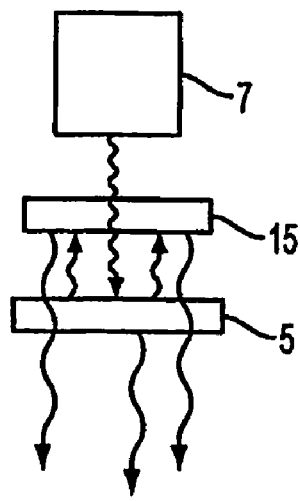

In a fourth embodiment of the present invention shown in FIG. 5, an optical filter 15 is located between the UV excitation source 7 and the UV light emitting device 5. The filter 15 is transparent to the shorter wavelength UV excitation radiation from source 7. However, the filter 15 reflects UV light of a longer peak wavelength emitted by the UV light emitting device 5. The filter 15 may be a holographic filter or any other suitable filter having the above described property. This configuration is advantageous when nanoparticles are used as the light emitting device 5. The nanoparticles emit UV light in all directions. However, the filter 15 reflects UV light emitted toward the source 7 back in the direction of the portion of the chamber 3 in which the person is to be located.

Figure 6:
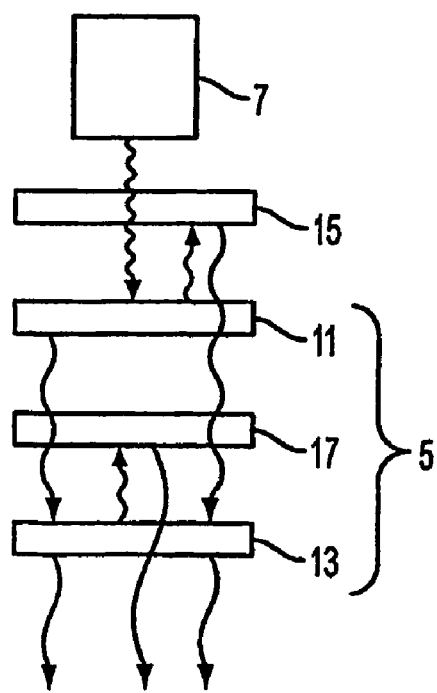

The fifth embodiment is a combination of the third and fourth embodiments. As shown in FIG. 6, the UV light emitting device 5 comprises a plurality of layers 11, 13 of nanoparticles or nanowires arranged in a direction extending from the UV excitation radiation source 7 to the portion of the chamber 3 which houses the person undergoing tanning or phototherapy. The nanoparticles or nanowires in each layer 11, 13 emit radiation having a different peak wavelength from the nanoparticles or nanowires in other layers. The peak wavelength of the UV radiation emitted by the nanoparticles or nanowires increases in each subsequent layer in the direction from the excitation radiation source 7 to the portion of the chamber 3 which houses the person undergoing tanning or phototherapy. A filter 17 is located between adjacent layers of nanoparticles or nanowires. The filter 17 is transparent to the shorter wavelength UV light from the layer 11 proximal to the UV excitation source 7. However, the filter 17 reflects UV light of a longer peak wavelength emitted by layer 13 distal from the UV excitation source 7. If the device 5 contains more than three layers of nanoparticles or nanowires, then a different filter may be located between each pairs of layers.

Figure 7:
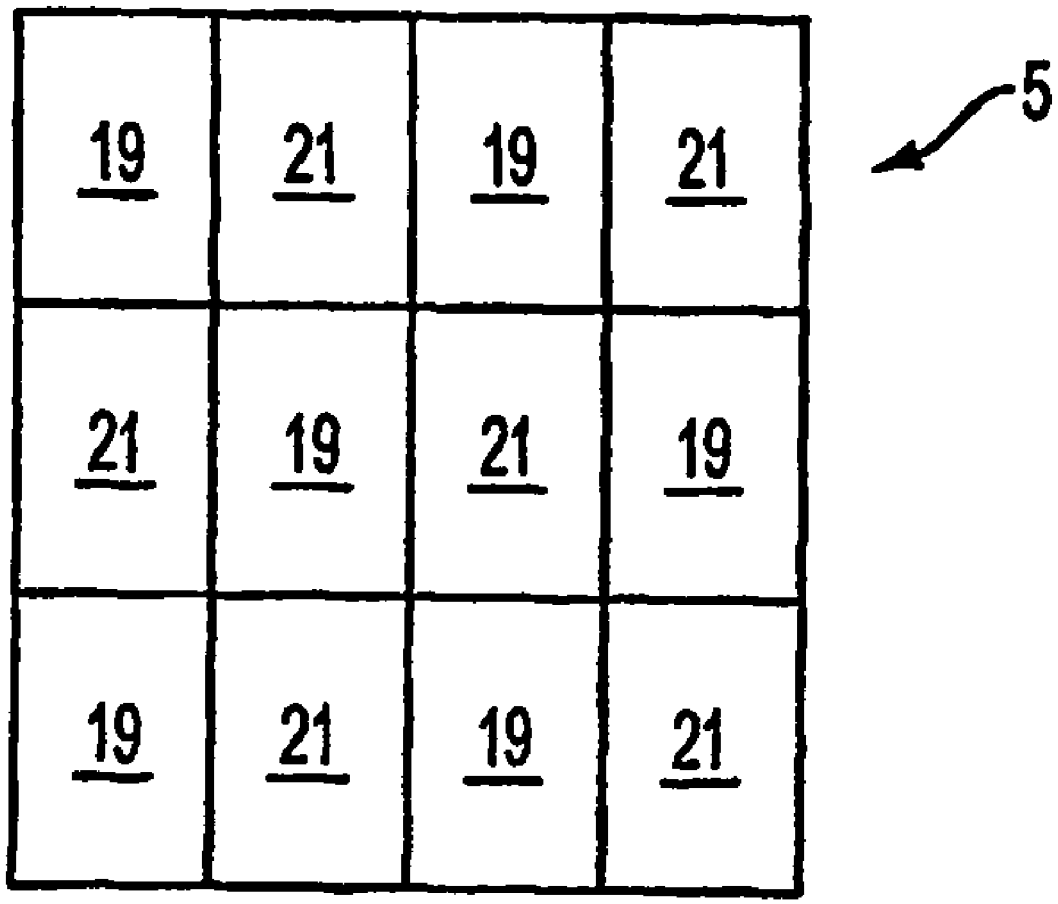
FIG. 7 is a bottom view of a nanostructure UV light emitting device according to an embodiment of the present invention.

In a sixth embodiment, the nanoparticles or nanowires are arranged in pixels as shown in FIG. 7. The nanoparticles or nanowires in each pixel can be separately activated by a dedicated UV excitation radiation source or by dedicated electrodes to selectively tan or treat a desired portion of skin on the person undergoing tanning or phototherapy. In one aspect of the sixth embodiment, the UV light emitting device 5 includes a first set of pixels 19 of first nanoparticles or nanowires. The first nanoparticles or nanowires are adapted to emit UV light having a predetermined first peak wavelength. The device 5 also includes a second set of pixels 21 of second nanoparticles or nanowires. The second nanoparticles or nanowires emit UV light of the second peak wavelength longer than the first peak wavelength. If desired, additional sets of pixels may be provided. Pixels of the first set of pixels 19 are interspersed with pixels of the second set of pixels 21.

All pixels may be turned on at once to provide UV light having a plurality of different peak wavelengths or one set of pixels may be selectively activated while the other sets remain turned off. In this case, the peak wavelength of the UV light may be selectively tailored for each individual based on the desired darkness of the tan, the individual's skin color or a selection of a particular wavelengths to treat a particular condition during phototherapy.

In a seventh embodiment, the system 1 contains the UV light emitting device 5 with exchangeable nanoparticles or nanowires to vary the peak emission wavelength of the device 5. For example, if the nanoparticles are located in a suspension in a sealed vessel, then the vessel may be opened and the suspension replaced by another suspension having nanoparticles which emit light of a different wavelength from the nanoparticles in the original suspension. Preferably, the vessel comprises non-stick surfaces to prevent nanoparticle adhesion. Alternatively, the entire vessel housing the suspension may be removed from the system and replaced with another vessel containing a different suspension of different nanoparticles which emit light of a different peak wavelength than the nanoparticles of the original suspension. If the nanoparticles or nanowires are coated as a solid layer on a substrate or substrates, then the substrate or substrate may be easily removable from the system to allow the system operator to insert a substrate or substrates containing nanoparticles or nanowires which emit light of a desired peak wavelength into the system 1.

A method of operating the system 1 for at least one of skin tanning and phototherapy includes providing UVA light from a nanostructure UV light emitting device 5 onto a skin of a human subject who is located in a chamber 3 adapted for at least one of skin tanning and phototherapy in order to at least one of tan the skin and to provide phototherapy for the skin. Phototherapy includes but is not limited to sleroderma therapy, psoriasis therapy, lupus therapy, photopheresia, and photochemotherapy.

The method also includes providing UV excitation radiation of a first peak wavelength from a UV excitation source 7 to the UV light emitting device 5. The method also includes emitting the UVA light having a second UVA peak wavelength longer than the first peak wavelength from the UV light emitting device 5 in response to the provided UV excitation radiation.

In an eighth embodiment, blue light having a wavelength of about 400 to about 415 nm, such as about 405 nm is used instead of UV light. Light of this wavelength is sometimes called violet or purple rather than blue. Any suitable blue or violet light emitting device 5 which emits light of this wavelength may be used, including a lamp, a light emitting diode, nanoparticle or nanowire containing device 5. The light emitting diode, nanoparticles and nanowires are preferred because they have a narrower emission peak width. For light emitting diodes, blue light emitting diodes based on GaN, SiC or ZnSe semiconductor materials may be used. Tanning with light in the 400-415 nm wavelength range may provide a longer lasting tan than tanning with UV light. Preferably but not necessarily, the light emitting device emits light having substantially no wavelengths outside the about 400 nm to the about 415 nm range, such as emitting less than 1% of light having wavelengths outside the about 400 nm to the about 415 nm range. The device 5 of this embodiment may be used in combination with the configuration(s) of the other embodiments described herein.

The foregoing description of the invention has been presented for purposes of illustration and description. It is not intended to be exhaustive or to limit the invention to the precise form disclosed, and modifications and variations are possible in light of the above teachings or may be acquired from practice of the invention. The drawings and description were chosen in order to explain the principles of the invention and its practical application. It is intended that the scope of the invention be defined by the claims appended hereto, and their equivalents.

What is claimed is:

1. A system for at least one of skin tanning and phototherapy, comprising:
    a chamber adapted for at least one of skin tanning and phototherapy; and
    a nanostructure UV light emitting device;
    wherein:
    a UV excitation source is positioned to provide a UV excitation radiation of a first peak wavelength onto the nanostructure UV light emitting device to cause the nanostructure UV light emitting device to emit UVA light having a second UVA peak wavelength longer than the first peak wavelength, wherein
    the nanostructure UV light emitting device comprises at least one of a nanoparticle or a nanowire device for emitting only UVA light.

2. The system of claim 1, wherein the system performs skin-tanning.

3. The system of claim 1, wherein the system performs phototherapy.

4. The system of claim 1, wherein the system performs both tanning and phototherapy.

5. The system of claim 1, wherein the chamber comprises a bed or a booth.

6. The system of claim 1, wherein the UV light emitting device comprises nanoparticles having an average diameter smaller than 100 nm or nanowires having an average thickness smaller than 150 nm.

7. The system of claim 1, wherein the UV light emitting device comprises a UVA-1 light emitting device and the nanoparticles emit only UVA-1 light due to their size.

8. The system of claim 1, wherein the UV light emitting device comprises:
    a first layer of first nanoparticles or nanowires located proximal to the UV excitation source, wherein the first nanoparticles or nanowires emit UV light of a third peak wavelength longer than the first peak wavelength when irradiated with the UV excitation radiation; and
    a second layer of second nanoparticles or nanowires located distal from the UV excitation source, such that the first layer is located between the second layer and the UV excitation source, wherein the second nanoparticles or nanowires emit UV light of the second peak wavelength longer than the third peak wavelength when irradiated with the UV light from the nanoparticles or nanowires of the first layer.

9. The system of claim 1, wherein:
    the UV excitation source comprises a gas vessel comprising a gas which is adapted to emits the UV excitation radiation in response to a stimulus; and
    the UV light emitting device comprises at least one layer of nanoparticles coated on an inner surface of at least one UV light transparent wall of the gas vessel.

10. The system of claim 1, wherein:
    the UV excitation source comprises a UV lamp; and
    the UV light emitting device comprises at least one layer of nanoparticles coated on an outer surface of the UV lamp.

* * * * *